United States Patent
Matsuishi et al.

(10) Patent No.: US 6,906,226 B2
(45) Date of Patent: Jun. 14, 2005

(54) HYDROXYMETHYL-SUBSTITUTED POLYFUNCTIONAL PHENOLS

(75) Inventors: Kazuya Matsuishi, Wakayama (JP); Takayuki Ohno, Wakayama (JP); Taiichi Shiomi, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 180 days.

(21) Appl. No.: 10/406,754

(22) Filed: Apr. 3, 2003

(65) Prior Publication Data

US 2003/0204117 A1 Oct. 30, 2003

(30) Foreign Application Priority Data

Apr. 8, 2002 (JP) ........................... 2002-105282

(51) Int. Cl.$^7$ ............................... C07L 39/12

(52) U.S. Cl. .................. 568/718; 568/721; 568/723; 568/726; 568/727

(58) Field of Search ................. 568/718, 721, 568/726, 723, 727

(56) References Cited

U.S. PATENT DOCUMENTS

| | | | | |
|---|---|---|---|---|
| 5,488,182 A | * | 1/1996 | Kobayashi et al. | .......... 568/660 |
| 2004/0023139 A1 | * | 2/2004 | Yoshimura et al. | ......... 430/59.6 |

OTHER PUBLICATIONS

S. Seito, et al., "Condensation Reactions of Formaldehyde with Phenols. VI. Isomeric Tetramethyloldihydroxydiphenylmethanes," vol. 49, No. 10, May 25, 1955 Chem. Abstr. 49:6889.

* cited by examiner

Primary Examiner—Michael L. Shippen
(74) Attorney, Agent, or Firm—Knobbe, Martens Olson & Bear LLP

(57) ABSTRACT

Hydroxymethyl-substituted polyfunctional phenols, expressed by the following structure:

General structure (I)

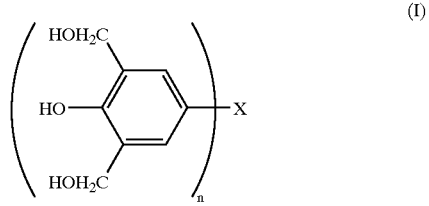

(I)

(wherein X represents: bivalent group (a) expressed by the following structure:

General structure (II)

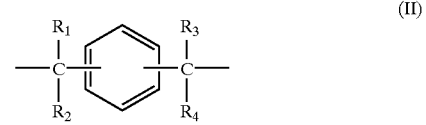

(II)

(wherein $R_1$, $R_2$, $R_3$ and $R_4$ each independently represent a hydrogen atom or an alkyl group with a carbon atom number of 1 through 4);

quadrivalent group (b) expressed by the following structure:

General structure (III)

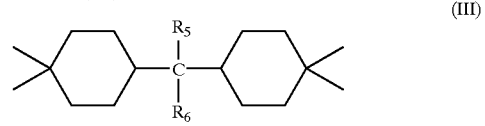

(III)

(wherein $R_5$ and $R_6$ each independently represent a hydrogen atom or an alkyl group with a carbon atom number of 1 through 4);

or bivalent group (c) expressed by the following structure:

General structure (IV)

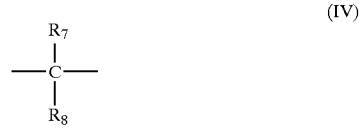

(IV)

(wherein $R_7$ and $R_8$ each independently represent a hydrogen atom or a monofluoromethyl, difluoromethyl or trifluoromethyl group; however, $R_7$ and $R_8$ cannot be both hydrogen atoms);

wherein n takes 2 when X is bivalent group (a), takes 4 when X is quadrivalent group (b), or takes 2 when X is bivalent group (c)).

4 Claims, No Drawings

HYDROXYMETHYL-SUBSTITUTED POLYFUNCTIONAL PHENOLS

BACKGROUND OF THE INVENTION

1. Field of the Invention

This invention relates to new hydroxymethyl-substituted polyfunctional phenols, wherein one phenol nucleus contains two hydroxymethyl groups as nucleus-substitution groups. Such compounds may be used as a modifier for phenol resins, etc., photo-resist material, or material for producing various polyphenol compounds involving chemical reaction of said compounds with phenols.

2. Description of the Related Art

The publication of Japanese Patent Application Laid-open No. 53-71044 discloses bis(4-hydroxy-3,5-dihydroxymethyl phenyl)methane, which is a bisphenol compound containing hydroxymethyl groups as nucleus-substitution groups. The publication of Japanese Patent Application Laid-open No. 8-277235 also discloses 3,3',5,5'-tetrahydroxymethyl-4,4'-diphenol as an intermediate material used for producing polyphenols via chemical reaction with phenols.

Among bisphenol compounds containing hydroxymethyl groups as nucleus-substitution groups, such as those mentioned above, polyfunctional phenols having an aromatic ring (e.g. benzene ring) or cycloalkane ring (e.g. cyclohexane ring) at the center of symmetry provide a high melting point. Polyphenol compounds made from these polyfunctional phenols are also expected to exhibit excellent resistance to heat. In addition, polyfunctional phenols having a fluorine-substituted alkylene group at the center of symmetry of the molecule are expected to offer property-modifying effects, such as improving the water repellency of phenol resins.

However, hydroxymethyl-substituted polyfunctional phenols, wherein the molecule of said phenol contains two or four phenol nucleuses each having two hydroxymethyl groups as nucleus-substitution groups and a benzene ring, cyclohexane ring or fluorine-substituted alkylene group at the center of symmetry of the module, have not heretofore been known.

SUMMARY OF THE INVENTION

In light of the aforementioned condition to date regarding hydroxymethyl-substituted polyfunctional phenols containing hydroxymethyl groups as nucleus-substitution groups, the present invention aims to provide new hydroxymethyl-substituted polyfunctional phenols, wherein the molecule of said phenol contains two or four phenol nucleuses each having two hydroxymethyl groups as nucleus-substitution groups and a benzene ring, cyclohexane ring or fluorine-substituted alkylene group at the center of symmetry of the module.

The present invention provides hydroxymethyl-substituted polyfunctional phenols expressed by the following structure:

General structure (I)

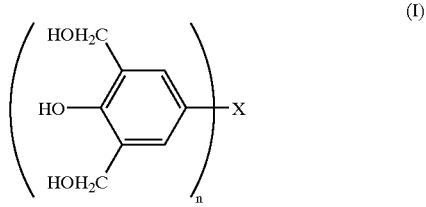

(wherein X represents: bivalent group (a) expressed by the following structure:

General structure (II)

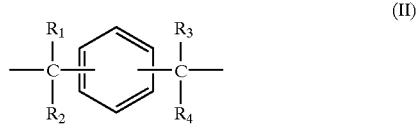

(wherein $R_1$, $R_2$, $R_3$ and $R_4$ each independently represent a hydrogen atom or an alkyl group with a carbon atom number of 1 through 4);

quadrivalent group (b) expressed by the following structure:

General structure (III)

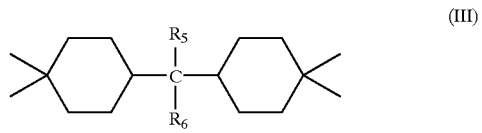

(wherein $R_5$ and $R_6$ each independently represent a hydrogen atom or an alkyl group with a carbon atom number of 1 through 4);

or bivalent group (c) expressed by the following structure:

General structure (IV)

(wherein $R_7$ and $R_8$ each independently represent a hydrogen atom or a monofluoromethyl, difluoromethyl or trifluoromethyl group; however, $R_7$ and $R_8$ cannot be both hydrogen atoms);

wherein n takes 2 when X is bivalent group (a), takes 4 when X is quadrivalent group (b), or takes 2 when X is bivalent group (c)).

DETAILED DESCRIPTION OF THE PREFERRED EMBODIMENT

The first type of new hydroxymethyl-substituted polyfunctional phenols provided by the present invention reflects aforementioned general structure (I), wherein X is bivalent group (a) expressed by aforementioned general structure (II). If $R_1$, $R_2$, $R_3$ and $R_4$ in bivalent group (a) are each an alkyl group with a carbon atom number of 1 through 4, specific examples of such alkyl groups include methyl, ethyl, propyl and butyl groups. Among these alkyl groups, propyl and butyl groups may have a linear or branched chain.

Therefore, 1,4-phenylenebis(methylidene) group, 1,4-phylenebis(1-ethylidene) group, 1,4-phenylenebis(1-propylidene) group, 1,4-phenylenebis(1-butylidene) group, 1,4-phenylenebis(2-methyl-1-propylidene) group, 1,4-phenylenebis(1-pentylidene) group, 1,4-phenylenebis(3-methyl-1-butylidene) group, 1,4-phenylenebis(3-methyl-1-butylidene) group, 1,4-phenylenebis(2,2-dimethyl-1-propylidene) group, 1,4-phenylenebis(1-methyl ethylidene) group, 1,4-phenylenebis(1-methyl propylidene) group, 1,4-phenylenebis(1-methyl butylidene) group, 1,4-phenylenebis (1-methyl pentylidene) group, 1,4-phenylenebis (1-ethyl propylidene) group, 1,4-phenylenebis(1-ethyl butylidene) group, 1,4-phenylenebis (1-ethyl pentylidene) group, 1,4-phenylenebis(1-propyl butylidene) group, 1,4-phenylenebis (1-isopropyl-2-methyl propylidene) group, 1,4-phenylenebis(1-propyl pentylidene) group, 1,4-phenylenebis(1-butyl pentylidene) group, 1,4-phenylenebis(1-t-butyl-2,2-dimethyl propylidene) group, 1,3-phenylenebis(methylidene) group, 1,3-phenylenebis(1-methyl ethylidene) group, 1,3-phenylenebis(1-ethyl propylidene) group, 1,3-phenylenebis(1-propyl butylidene) group and 1,3-phenylenebis(1-butyl pentylidene) group are given as specific examples of bivalent group (a) expressed by aforementioned general structure (II).

Therefore, 4,4'-[1,4-phenylenebis(methylidene)]bis(3,5-dihydroxymethyl phenol), 4,4'-[1,4-phenylenebis(1-ethylidene)]bis(3,5-dihydroxymethyl phenol), 4,4'-[1,4-phenylenebis(1-propylidene)]bis(3,5-dihydroxymethyl phenol), 4,4'-[1,4-phenylenebis(1-butylidene)]bis(3,5-dihydroxymethyl phenol), 4,4'-[1,4-phenylenebis(1-pentylidene)]bis (3,5-dihydroxymethyl phenol), 4,4'-[1,4-phenylenebis(1-methyl ethylidene)]bis(3,5-dihydroxymethyl phenol), 4,4'-[1,4-phenylenebis(1-ethyl propylidene)]bis(3,5-dihydroxymethyl phenol), 4,4'-[1,4-phenylenebis(1-propyl butylidene)]bis(3,5-dihydroxymethyl phenol), 4,4'-[1,4-phenylenebis(1-butyl pentylidene)]bis(3,5-dihydroxymethyl phenol), 4,4'-[1,3-phenylenebis(methylidene)]bis(3,5-dihydroxymethyl phenol), 4,4'-[1,3-phenylenebis(1-methyl ethylidene)]bis (3,5-dihydroxymethyl phenol), 4,4'-[1,3-phenylenebis(1-ethyl propylidene)]bis(3,5-dihydroxymethyl phenol), 4,4'-[1,3-phenylenebis(1-propyl butylidene)]bis(3,5-dihydroxymethyl phenol) and 4,4'-[1,3-phenylenebis(1-butyl pentylidene)]bis(3,5-dihydroxymethyl phenol) are given as specific examples of the first type of new hydroxymethyl-substituted polyfunctional phenols provided by the present invention.

The second type of new hydroxymethyl-substituted polyfunctional phenols provided by the present invention reflects aforementioned general structure (I), wherein X is quadrivalent group (b) expressed by aforementioned general structure (III). If $R_5$ and $R_6$ in quadrivalent group (b) are each an alkyl group with a carbon atom number of 1 through 4, specific examples of such alkyl groups include methyl, ethyl, propyl and butyl groups. Among these alkyl groups, propyl and butyl groups may have a linear or branched chain.

Therefore, methylidene group, 1-ethylidene group, 1-propylidene group, 1-butylidene group, 2-methyl-1-propylidene group, 1-pentylidene group, 3-methyl-1-butylidene group, 2,2-dimethyl-1-propylidene group, 1-methyl ethylidene group, 1-methyl propylidene group, 1-methyl butylidene group, 1-methyl pentylidene group, 1-ethyl propylidene group, 1-ethyl butylidene group, 1-ethyl pentylidene group, 1-propyl butylidene group, 1-isopropyl-2-methyl propylidene group, 1-propyl pentylidene group, 1-butyl pentylidene group and 1-t-butyl-2,2-dimethyl propylidene group are given as specific examples of quadrivalent group (b) expressed by aforementioned general structure (III).

Therefore, 1,1-bis [4,4-cyclohexylidenebis(4-hydroxy-3,5-dihydroxymethyl phenyl)]methane, 1,1-bis [4,4-cyclohexylidenebis(4-hydroxy-3,5-dihydroxymethyl phenyl)]ethane, 2,2-bis [4,4-cyclohexylidenebis(4-hydroxy-3,5-dihydroxymethyl phenyl)]propane, 1,1-bis [4,4-cyclohexylidenebis(4-hydroxy-3,5-dihydroxymethyl phenyl)]-1-methyl propane, 1,1-bis [4,4-cyclohexylidenebis(4-hydroxy-3,5-dihydroxymethyl phenyl)]-1-ethyl propane, 1,1-bis [4,4-cyclohexylidenebis(4-hydroxy-3,5-dihydroxymethyl phenyl)]-1-propyl butane, 1,1-bis [4,4-cyclohexylidenebis(4-hydroxy-3,5-dihydroxymethyl phenyl)]-1-isopropyl-2-methyl propane, 1,1-bis [4,4-cyclohexylidenebis(4-hydroxy-3,5-dihydroxymethyl phenyl)]-1-butyl pentane and 1,1-bis [4,4-cyclohexylidenebis(4-hydroxy-3,5-dihydroxymethyl phenyl)]-1-t-butyl-2,2-dimethyl propane are given as specific examples of the second type of new hydroxymethyl-substituted polyfunctional phenols provided by the present invention.

Further, the third type of new hydroxymethyl-substituted polyfunctional phenols provided by the present invention reflects aforementioned general structure (I), wherein X is bivalent group (c) expressed by aforementioned general structure (IV). $R_7$ and $R_8$ in bivalent group (c) are each an independent hydrogen atom or a monofluoromethyl group, difluoromethyl group or trifluoromethyl group. However, $R_7$ and $R_8$ cannot be both hydrogen atoms.

Therefore, 2-fluoroethylidene group, 2-difluoroethylidene group, 2-trifluoroethylidene group, 1-fluoromethyl-2-fluoroethylidene group, 1-fluoromethyl-2-difluoroethylidene group, 1-difluoromethyl-2-difluoroethylidene group and 1-trifluoromethyl-2-trifluoroethylidene group are given as specific examples of aforementioned bivalent group (c).

Therefore, 4,4'-(2-fluoroethylidene)bis(3,5-dihydroxymethyl phenol), 4,4'-(2-difluoroethylidene)bis(3,5-dihydroxymethyl phenol), 4,4'-(2-trifluoroethylidene)bis(3,5-dihydroxymethyl phenol), 4,4'-(1-fluoromethyl-2-fluoroethylidene)bis(3,5-dihydroxymethyl phenol), 4,4'-(1-difluoromethyl-2-difluoroethylidene)bis(3,5-dihydroxymethyl phenol) and 4,4'-(1-trifluoromethyl-2-trifluoroethylidene)bis(3,5-dihydroxymethyl phenol) are given as specific examples of the third type of new hydroxymethyl-substituted polyfunctional phenols provided by the present invention.

The hydroxymethyl-substituted polyfunctional phenols provided by the present invention, which are expressed by aforementioned general structure (I), may be obtained from multivalent phenol compounds expressed by general structure (V) below:

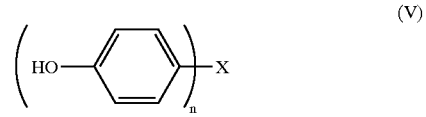

(V)

(wherein X and n are the same as defined earlier).

To be specific, each multivalent phenol compound of the above structure is reacted with 1 to 10 mols, or preferably 1.5 to 5 mols, of formaldehyde per 1 mol of hydroxymethyl group contained in 1 mol of the target substance, in the presence of basic catalyst or in water or a mixed solvent consisting of water and organic solvent, after which the obtained reaction product is neutralized.

The amount of formaldehyde will significantly exceed the theoretical value in this reaction, if more than 10 mols of formaldehyde is reacted with the aforementioned multivalent phenol compound per 1 mol of hydroxymethyl group contained in 1 mol of the target substance, and therefore the process economy will drop. On the other hand, it is equally undesirable to react less than 10 mols of formaldehyde with the aforementioned multivalent phenol compound per 1 mol of hydroxymethyl group contained in 1 mol of the target substance, since a significant amount of monohydroxymethyl-group substitution products or unreacted bisphenols will remain.

The formaldehyde used in the aforementioned production method may be a commercially available, undiluted formalin solution. Alternatively, paraformaldehyde or trioxane that reacts in a similar manner to formaldehyde in water can also be used. However, use of formalin is preferred.

The aforementioned basic catalyst may be a hydroxide of alkali metal such as sodium hydroxide, potassium hydroxide or lithium hydroxide, acetate, calcium hydroxide, or a bivalent metal such as zinc hydroxide or magnesium hydroxide. However, use of a hydroxide of alkaline earth, acetate, pyridine, or a Class 3 amine such as trimethyl amine or tributyl amine is preferred. Among these, sodium hydroxide or potassium hydroxide is most preferred.

In the present invention, such basic catalyst may be added by an equivalent of 0.1 to 5 times, or preferably 0.1 to 2 times, the hydroxyl amount in the aforementioned multivalent phenol compound. If the amount of basic catalyst exceeds 5 times the hydroxyl amount in the aforementioned multivalent phenol compound, the basic catalyst becomes excessive in the reaction system. This is not desirable, since an excessively large amount of acid will be required to acidify the reaction system for precipitation and collection of the reaction production.

In the present invention, the reaction of the above multivalent phenol compound and formaldehyde in the presence of basic catalyst is normally initiated in a water medium or a mixed solvent consisting of water and organic solvent. The amount of water/mixed solvent is normally around 1 to 5 times, or preferably 2 to 3 times, the weight of the reacting material, which, in this case, is the above multivalent phenol compound.

The aforementioned organic solvent may be an alcohol solvent such as methanol, ethanol, n-propyl alcohol, isopropyl alcohol, n-butanol, ethylene glycol, ethylene glycol monomethyl ether, diethylene glycol or carbitol, or a water-soluble organic solvent such as tetrahydrofuran, dioxane, dimethyl formamide, dimethyl acetamide or n-methyl pyrolidone, as long as the solubility, in the mixed solvent, of the aforementioned basic catalyst and the reacting material, which, in this case, is the aforementioned multivalent phenol compound, will not be affected.

The above reaction is normally initiated in a temperature range of 0 to 60° C., or preferably 30 to 50° C., over a period of around 1 to 72 hours, or preferably 4 to 16 hours. A reaction temperature exceeding 60° C. will produce large amounts of various unwanted byproducts, such as the substances with high molecular weight mentioned earlier.

The product obtained from said condensation reaction of the aforementioned multivalent phenol compound and formaldehyde in the presence of basic catalyst is a mixture containing said multivalent phenol compound having hydroxymethyl groups added to the aromatic nucleuses on both sides of its molecule. This molecular structure exists in the obtained reaction mixture partially or entirely as alkali salt, depending on the amount of basic catalyst used. This reaction is generally a solution reaction, although the specific form of reaction varies depending on the type and content of alcohol or other organic solvent in the water medium or mixed solvent used for reaction, amount of water medium/mixed solvent used, and type and amount of basic catalyst used.

Therefore, to separate and collect the target reaction product from the obtained reaction mixture, in the present invention the obtained reaction mixture is cooled and mixed with an extractant, which may be an organic, water-insoluble solvent such as any of the aromatic hydrocarbons, fatty alcohols, aliphatic ketones or esters, or any combination of such solvents. The reaction mixture with extractant is then added to an acid compound, such as organic acid, inorganic acid or water solution of such acid, to neutralize the entire reaction mixture and thereby separate the water layer and extract the reaction product into the organic layer. Next, thus obtained organic layer is condensed as necessary and then cooled to cause precipitation. Finally, the solid precipitate is filtered to obtain a hydroxymethyl-substituted polyfunctional phenol, which is the target substance.

In the present invention, an extractant can also be added after the reaction mixture is neutralized. In particular, the present invention provides a hydroxymethyl-substituted polyfunctional phenol of even higher purity by removing in advance the impurities separating from the reaction mixture using the aforementioned extractant in an early stage of neutralization, extracting the reaction product from the water layer into the organic layer using the aforementioned extractant, and then processing the organic layer as described above.

The aforementioned extractant may be any of the aromatic hydrocarbons such as benzene, toluene or xylene, fatty alcohols such as n-butanol, aliphatic ketones such as methyl isobutyl ketone or esters such as ethyl acetate or butyl acetate, which may be used alone or in combination.

Of the acid compounds that may be used in the aforementioned neutralization process, those that are organic acids include formic acid, acetic acid, proprionic acid and oxalic acid. Inorganic acids include sulfuric acid, phosphoric acid, phosphorous acid, hypophosphorous acid and hydrochloric acid. Of these, use of hydrochloric acid and sulfuric acid is most preferred from the viewpoint of economy and ease of handling.

The chemical compounds obtained by the present invention using the method described above are normally in a solid state at normal temperature, and therefore can be used for various applications. In particular, the compounds provided by the present invention can be used as photo-resist material or to derive polyphenol compounds through further reaction with phenolic compounds. The compounds provided by the present invention are also usable as compounding agent that adds to the molecular weight of novolac phenol resins or as hardening agent for epoxy resins used in casting and powder coating. In these applications, the desired effect manifests after reaction with hydroxymethyl groups.

EXAMPLES

The present invention is explained by using examples. However, application of the present invention is not limited to the examples provided.

Example 1

Production of 4,4'-[1,4-phenylenebis(1-methyl ethylidene)]bis(3,5-dihydroxymethyl phenol)

51.9 g (0.15 mol) of 4,4'-[1,4-phenylenebis(1-methyl ethylidene)]bisphenol, 10.8 g (0.45 mol) of lithium hydroxide and 176 g of pure water were mixed into a four-neck flask and agitated at room temperature for 10 minutes. Into the obtained solution kept at 40° C., 154 g (1.80 mol) of 35% formaldehyde solution was dropped to cause reaction over 2 hours. The reacted solution was kept at the same temperature for another 20 hours for thorough reaction.

At the end of the reaction period, the obtained reaction mixture (solution) was neutralized by adding 16% sulfuric acid, after which n-butyl alcohol was added to dissolve the reaction product. Thereafter, the water layer was separated and the obtained oil layer was rinsed in water. The oil layer was then distilled to obtain 77.2 g of the target substance in coarse state (63.5% purity as measured by high-speed liquid chromatography) as a light yellowish-brown solution. The solution was then refined by column chromatography to obtain the target 4,4'-[1,4-phenylenebis(1-methyl ethylidene)]bis(3,5-dihydroxymethyl phenol) as a white solid with 98% purity.

Mass spectrometry (LC-MS/AP): 466

Proton nuclear magnetic resonance spectrum (400 MHz, solvent: DMSO):

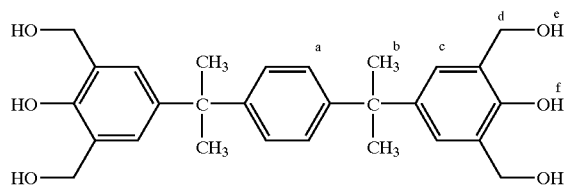

TABLE 1

| δ (ppm) | Signal | Number of protons | Assignment |
| --- | --- | --- | --- |
| 1.58 | s | 12 | b |
| 4.52 | s | 8 | d |
| 5.24 | s | 4 | e |
| 7.05 | s | 4 | c |
| 7.08 | s | 4 | a |
| 8.40 | s | 2 | f |

Example 2

Production of 4,4'-[1,3-phenylenebis(1-methyl ethylidene)]bis(3,5-dihydroxymethyl phenol)

69.2 g (0.20 mol) of 4,4'-[1,3-phenylenebis(1-methyl ethylidene)]bisphenol, 150 g (0.60 mol) of 16% sodium hydroxide solution and 34.6 g of methanol were mixed into a four-neck flask and agitated at room temperature for 10 minutes. Into the obtained solution kept at 30° C., 205.7 g (2.4 mol) of 35% formaldehyde solution was dropped to cause reaction over 2 hours. The reacted solution was kept at the same temperature for another 7 hours for thorough reaction.

At the end of the reaction period, the obtained reaction mixture (solution) was neutralized by adding 16% sulfuric acid, after which n-butyl alcohol was added to dissolve the reaction product. Thereafter, the water layer was separated and the obtained oil layer was rinsed in water. The oil layer was then distilled to obtain 131 g of the target substance in coarse state (83.6% purity as measured by high-speed liquid chromatography) as a light yellow solution. The solution was then refined by column chromatography to obtain the target 4,4'-[1,3-phenylene bis(1-methyl ethylidene)]bis(3,5-dihydroxymethyl phenol) as a light brown solution with 98% purity.

Mass spectrometry (LC-MS/AP): 466

Proton nuclear magnetic resonance spectrum (400 MHz, solvent: DMSO):

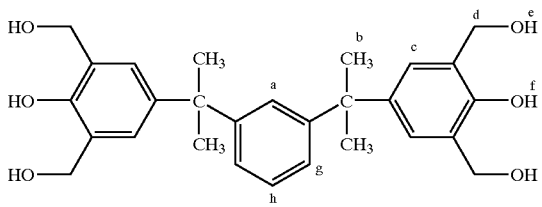

TABLE 2

| δ (ppm) | Signal | Number of protons | Assignment |
| --- | --- | --- | --- |
| 1.56 | s | 12 | b |
| 4.52 | s | 8 | d |
| 5.26 | s | 4 | e |
| 6.94 | d | 2 | g |
| 7.01 | s | 4 | c |
| 7.11 | t | 1 | h |
| 7.22 | s | 1 | a |
| 8.40 | s | 2 | f |

Example 3

Production of 2,2-bis [4,4-cyclohexylidenebis(4-hydroxy-3,5-dihydroxymethyl phenyl)]propane 86.4 g (0.15 mol) of 2,2-bis [4,4-cyclohexylidenebis(4-hydroxy phenyl)]propane and 225 g (0.9 mol) of 16% sodium hydroxide solution were mixed into a four-neck flask and agitated at room temperature for 10 minutes. Into the obtained solution kept at 20° C., 321.4 g (3.75 mol) of 35% formaldehyde solution was dropped to cause reaction over approximately 1.7 hours. The reacted solution was kept at the same temperature for another 16.5 hours for thorough reaction.

At the end of the reaction period, the obtained reaction mixture (solution) was neutralized by adding 16% sulfuric acid, after which methyl ethyl ketone was added to dissolve the reaction product. Thereafter, the water layer was separated and the obtained oil layer was rinsed in water. The oil layer was then distilled to obtain 90 g of the target substance in coarse state (57.1% purity as measured by high-speed liquid chromatography) as a white solid. The solid was dissolved in methanol and refined by column chromatography to obtain the target 2,2-bis [4,4-cyclohexylidenebis(4-hydroxy-3,5-dihydroxymethyl phenyl)]propane as a white solid with 93% purity.

Mass spectrometry (LC-MS/AP): 816

Proton nuclear magnetic resonance spectrum (400 MHz, solvent: DMSO):

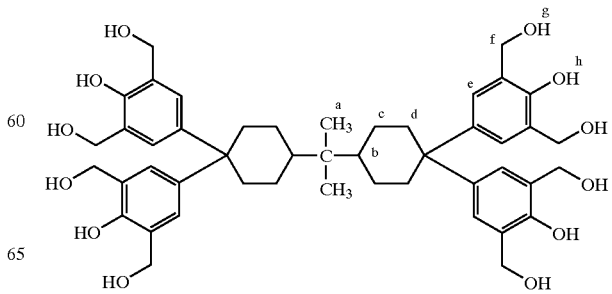

TABLE 3

| δ (ppm) | Signal | Number of protons | Assignment |
|---|---|---|---|
| 0.47 | s | 6 | a |
| 1.09 | t | 4 | c |
| 1.33 | t | 2 | b |
| 1.53 | d | 4 | c |
| 1.69 | t | 4 | d |
| 2.69 | d | 4 | d |
| 4.46 to 4.53 | d | 16 | f |
| 5.19 to 5.27 | t | 8 | g |
| 6.99 | s | 8 | e |
| 7.13 | | | |
| 8.30 | s | 4 | h |
| 8.34 | | | |

Example 4

Production of 4,4'-(1-trifluoromethyl-2-trifluoroethylidene)bis(3,5-dihydroxymethyl phenol)

168 g (0.5 mol) of 4,4'-[1-trifluoromethyl-2-trifluoroethylidene]bisphenol and 280.3 g (1.0 mol) of 20% potassium hydroxide solution were mixed into a four-neck flask and agitated at room temperature for 10 minutes. Into the obtained solution kept at 50° C., 342.9 g (4.0 mol) of 35% formaldehyde solution was dropped to cause reaction over approximately 1.5 hours. The reacted solution was kept at the same temperature for another 14.5 hours for thorough reaction.

At the end of the reaction period, the obtained reaction mixture (solution) was neutralized by adding 16% sulfuric acid, after which methyl isobutyl ketone was added to dissolve the reaction product. Thereafter, the water layer was separated and the obtained oil layer was rinsed in water. The oil layer was then distilled to obtain a concentrate. The concentrate was recrystallized by adding toluene and methanol, then filtered and dried to obtain 125 g of the target 4,4'-(1-trifluoromethyl-2-trifluoroethylidene)bis(3,5-dihydroxymethyl phenol) in refined state (94.1% purity as measured by high-speed liquid chromatography) as a white solid.

Melting point: 155.2° C.

Mass spectrometry (LC-MS/AP): 456

Proton nuclear magnetic resonance spectrum (400 MHz, solvent: DMSO):

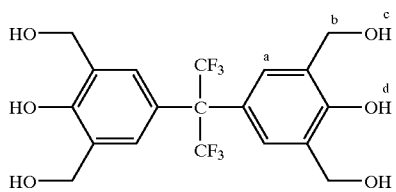

TABLE 4

| δ (ppm) | Signal | Number of protons | Assignment |
|---|---|---|---|
| 4.54 | s | 8 | b |
| 5.36 | s | 4 | c |
| 7.20 | s | 4 | a |
| 8.91 | s | 2 | d |

What is claimed is:

1. Hydroxymethyl-substituted polyfunctional phenols, expressed by the following structure:

General structure (I)

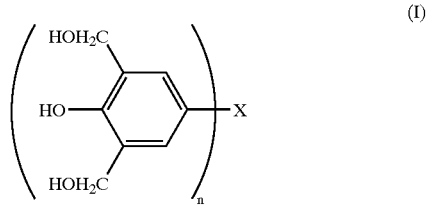

(wherein X represents bivalent group (a) expressed by the following structure:

General structure (II)

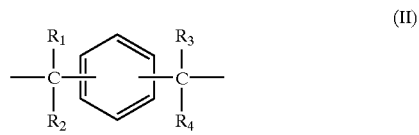

(wherein $R_1$, $R_2$, $R_3$ and $R_4$ each independently represent a hydrogen atom or an alkyl group with a carbon atom number of 1 through 4);

quadrivalent group (b) expressed by the following structure:

General structure (III)

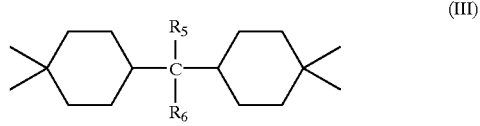

(wherein $R_5$ and $R_6$ each independently represent a hydrogen atom or an alkyl group with a carbon atom number of 1 through 4);

or bivalent group (c) expressed by the following structure:

General structure (IV)

(wherein $R_7$ and $R_8$ each independently represent a hydrogen atom or a monofluoromethyl, difluoromethyl or trifluoromethyl group; however, $R_7$ and $R_8$ cannot be both hydrogen atoms);

wherein n takes 2 when X is bivalent group (a), takes 4 when X is quadrivalent group (b), or takes 2 when X is bivalent group (c)).

2. The hydroxymethyl-substituted polyfunctional phenols as recited in claim 1, wherein said $R_1$, $R_2$, $R_3$ and $R_4$ in General structure (II) each independently represent a methyl group, an ethyl group, a propyl group or a butyl group.

3. The hydroxymethyl-substituted polyfunctional phenols as recited in claim 1, wherein said $R_5$ and $R_6$ in General structure (III) each independently represent a methyl group, an ethyl group, a propyl group or a butyl group.

4. A method for producing hydroxymethyl-substituted polyfunctional phenols, expressed by the following structure:

General structure (I)

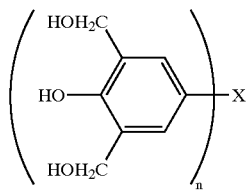

(I)

(wherein X represents: bivalent group (a) expressed by the following structure:

General structure (II)

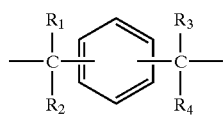

(II)

(wherein $R_1$, $R_2$, $R_3$ and $R_4$ each independently represent a hydrogen atom or an alkyl group with a carbon atom number of 1 through 4);

quadrivalent group (b) expressed by the following structure:

General structure (III)

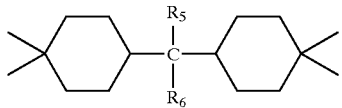

(III)

(wherein $R_5$ and $R_6$ each independently represent a hydrogen atom or an alkyl group with a carbon atom number of 1 through 4);

or bivalent group (c) expressed by the following structure:

General structure (IV)

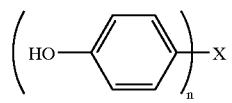

(IV)

(wherein $R_7$ and $R_8$ each independently represent a hydrogen atom or a monofluoromethyl, difluoromethyl or trifluoromethyl group; however, $R_7$ and $R_8$ cannot be both hydrogen atoms);

wherein n take 2 when X is bivalent group (a), takes 4 when X is quadrivalent group (b), or takes 2 when X is bivalent group (c)), said method comprising the steps of:

reacting multivalent phenol compounds expressed by general structure (V) below

(V)

(wherein X and n are the same as defined earlier)

with 1 to 10 mols of formaldehyde per 1 mol of hydroxymethyl group contained in 1 mol of the target substance, in water or a mixed solvent consisting of water and organic solvent, in the presence of basic catalyst; and neutralizing the obtained reaction product to produce hydroxymethyl-substituted polyfunctional phenols.

* * * * *